United States Patent
Worms et al.

(10) Patent No.: US 11,309,614 B2
(45) Date of Patent: Apr. 19, 2022

(54) DEVICE FOR TRANSMITTING A SIGNAL WITH THE AID OF WAVEGUIDES

(71) Applicant: Robert Bosch GmbH, Stuttgart (DE)

(72) Inventors: Kai Worms, Hardthausen Am Kocher (DE); Ludwig Brechter, Eberdingen (DE)

(73) Assignee: Robert Bosch GmbH, Stuttgart (DE)

( * ) Notice: Subject to any disclaimer, the term of this patent is extended or adjusted under 35 U.S.C. 154(b) by 29 days.

(21) Appl. No.: 16/965,891

(22) PCT Filed: Jan. 17, 2019

(86) PCT No.: PCT/EP2019/051149
§ 371 (c)(1),
(2) Date: Jul. 29, 2020

(87) PCT Pub. No.: WO2019/149535
PCT Pub. Date: Aug. 8, 2019

(65) Prior Publication Data
US 2021/0005944 A1 Jan. 7, 2021

(30) Foreign Application Priority Data
Feb. 1, 2018 (DE) .......................... 102018201510.4

(51) Int. Cl.
*H01P 1/06* (2006.01)
*H01P 3/08* (2006.01)

(52) U.S. Cl.
CPC .............. *H01P 1/068* (2013.01); *H01P 3/081* (2013.01)

(58) Field of Classification Search
CPC .... H01P 1/06; H01P 1/068; H01P 3/08; H01P 5/02
See application file for complete search history.

(56) References Cited

U.S. PATENT DOCUMENTS

| | | | | |
|---|---|---|---|---|
| RE29,975 E | * | 4/1979 | Ishigaki | H04N 9/84 386/269 |
| 4,730,224 A | * | 3/1988 | Komatsu | H01P 1/068 333/261 |

(Continued)

FOREIGN PATENT DOCUMENTS

| | | |
|---|---|---|
| CN | 101036583 A | 9/2007 |
| CN | 102133105 A | 7/2011 |

(Continued)

OTHER PUBLICATIONS

International Search Report dated Apr. 10, 2019 in connection with PCT/EP2019/051149.

*Primary Examiner* — Dean O Takaoka
(74) *Attorney, Agent, or Firm* — Norton Rose Fulbright US LLP; Gerard Messina

(57) ABSTRACT

A device for transmitting a signal with the aid of waveguides in rotating systems. The device includes at least one transmitting waveguide and at least one receiving waveguide. The at least one receiving waveguide and the at least one transmitting waveguide being divided into multiple radially distributed segments. The radially distributed segments of the at least one receiving waveguide each include a tap. An adder for adding the signals obtained with the aid of the taps of the radially distributed segments of the at least one receiving waveguide is also provided.

14 Claims, 2 Drawing Sheets

(56) References Cited

U.S. PATENT DOCUMENTS

| | | | | |
|---|---|---|---|---|
| 4,904,919 | A | * | 2/1990 | McNaughton .......... H02P 27/08 |
| | | | | 318/798 |
| 5,192,923 | A | * | 3/1993 | Komatsu ................. H01P 1/068 |
| | | | | 333/116 |
| 6,181,766 | B1 | | 1/2001 | Pearson, Jr. et al. |
| 2004/0116099 | A1 | | 6/2004 | Schilling et al. |
| 2005/0052006 | A1 | | 3/2005 | Nishimura et al. |

FOREIGN PATENT DOCUMENTS

| | | | |
|---|---|---|---|
| CN | 104346912 A | | 2/2015 |
| CN | 106526686 A | | 3/2017 |
| DE | 19533820 A1 | | 3/1996 |
| DE | 19543559 A1 | | 5/1997 |
| DE | 19543558 B4 | | 3/2005 |
| DE | 102011050588 A1 | | 11/2012 |
| EP | 0093468 A1 | | 11/1983 |
| JP | 63220401 A | * | 9/1988 |
| JP | S63220401 A | | 9/1988 |
| JP | 04006904 A | * | 1/1992 |
| WO | 2015094802 A1 | | 6/2015 |

\* cited by examiner

DEVICE FOR TRANSMITTING A SIGNAL WITH THE AID OF WAVEGUIDES

FIELD

The present invention relates to a device for transmitting a signal with the aid of waveguides in rotating systems, including at least one transmitting waveguide and at least one receiving waveguide, the at least one transmitting waveguide and the at least one receiving waveguide being divided into multiple radially distributed segments.

BACKGROUND INFORMATION

Data transmissions between a continuously rotating area and a stationary area are needed in a wide variety of applications. Wind energy plants, computer tomographs, robots, and rotating laser radars shall be mentioned as examples. For data rates starting at several Mbit/s, wear-free, contactless methods are superior to the methods using traditional slip rings. One possible contactless method is based on the data transmission in the near field of mutually opposing waveguides.

The principle of such a transmission method is described in German Patent Application No. DE 195 43 558 B4, for example. A signal source is connected to a transmitting waveguide pair in the process, a signal to be transmitted being electromagnetically overcoupled to a second waveguide pair extending in parallel, which thus serves as a receiver. The waveguide pair of the receiver is typically shorter than that of the transmitter. To achieve a transmission which is immune to electromagnetic radiation, and moreover emits little electromagnetic radiation in the far field, a symmetrical design of the transmitter and receiver is typically selected. This means that the path of the current toward the receiver and its return path lead over identically designed structures. Accordingly, the two waveguides of the waveguide pair for transmitting and the two waveguides of the waveguide pair for receiving each must have the same surface area.

Furthermore, a signal curve of a waveguide coupler is described in German Patent Application No. DE 195 43 559 A1, which is shown in various locations during the transmission. Accordingly, an input data signal has a rectangular shape, the edge steepness of this signal being increased with the aid of a comparator. With the aid of the equation $\lambda_{min} = c2\pi\tau$, it is possible to estimate the lowest relevant wavelength $\lambda_{min}$ based on the rise time $\tau$ of the edge and the propagation velocity c of the wave. As a result of the electromagnetic coupling of the transmitting waveguide pair to the receiving waveguide pair, a high pass filtering of the input signal takes place, which results in an output signal made up of pulses which occur in the area of the signal edges of the input signal. After passing through the waveguide coupler, the rectangular signal is restored by an integrator or a comparator with hysteresis.

Furthermore, a rotary transmitter based on waveguides is described in German Patent Application No. DE 195 33 820 B4, in which a data transmission functions for any angle of the receiver to the transmitter. To prevent reflections caused by a signal to be transmitted, the waveguides have a defined impedance, to which the rotary transmitter is set with the aid of matching resistors. Furthermore, reflections in the receiving antennas are avoided in that these are implemented considerably shorter than the smallest occurring wavelength $\lambda_{min}$.

According to the related art, a particularly simple design of a system for rotary transmission is provided in the form of two mutually opposing circuit boards, used waveguides being designed in the form of microstrip lines.

It is a drawback of the aforementioned conventional approaches from the related art that present waveguide rotary transmitters include a receiving waveguide which is considerably shorter than the smallest wavelength $\lambda_{min}$ occurring in the signal. In this way, the receiving waveguide is considerably smaller at high transmission rates than the circumference of the transmitting waveguide. Due to the resulting small coupling surface, the coupling efficiency is so low that additional amplifiers are required at the transmitter and the receiver. This increases the radiation of the transmitter on the one hand, and the costs and the energy consumption of the waveguide rotary transmitter on the other hand.

Another disadvantage of such a system is that the received signal amplitude is dependent on the distance between the receiving waveguide and the transmitting waveguide. If the system is designed in the form of two mutually opposing circuit boards, even a slight tilting of the circuit boards with respect to one another or an unevenness of one circuit board causes the signal amplitude to vary so drastically during one revolution that errors in the data transmission occur intermittently, depending on the rotation angle.

Based on feedback mechanisms, the receiver may compensate for the varying signal amplitude. This is described in U.S. Patent Application Publication No. US 2004/0116099 A1, for example, corresponding to a preferred method, the use of an amplifier including a settable amplification being provided. Such an amplifier, however, is cost-intensive and requires a lot of energy.

SUMMARY

According to the present invention, a device for transmitting a signal with the aid of waveguides in rotating systems is thus provided. In accordance with an example embodiment of the present invention, the device includes at least one transmitting waveguide and at least one receiving waveguide, the at least one receiving waveguide being divided into multiple radially distributed segments. The example device according to the present invention includes that the radially distributed segments of the at least one receiving waveguide each include a tap, and means for adding (e.g., an adder) the signals obtained with the aid of the taps of the radially distributed segments of the at least one receiving waveguide are provided.

The waveguides may preferably be coupled waveguides, particularly preferably coupled waveguides in an inhomogeneous dielectric being used.

The example waveguide rotary transmitter obtained according to the present invention has the advantage that it is largely immune to unevenness and tilting. This is achieved in that the receiving waveguide is divided into multiple, radially distributed segments, whose received signals are added up.

By adding up the signals of all receiving waveguides, the amplitude of the result becomes independent of the angular position, by which a cumbersome readjustment of the signal amplitude at the receiver is rendered unnecessary.

According to one preferred embodiment of the present invention, it is provided that the taps of the radially distributed segments of the at least one receiving waveguide are situated opposite one another. In this way, it is made possible that the receiving amplitude of a segment, which is reduced due to tilting or an unevenness, may be compensated for by another receiving amplitude of the opposite segment, which, in contrast, is high.

The device advantageously includes means for coupling the signal to be transmitted having positive polarity into a first segment of the at least one transmitting waveguide, and for coupling the signal to be transmitted having negative polarity into a second segment of the at least one transmitting waveguide. It is preferably provided in the process that a comparator is provided as the means for coupling the signal to be transmitted, which has a non-inverting output and an inverting output. In this way, it is achieved that the non-inverting output couples a rectangular input signal having positive polarity into a first transmitting waveguide, and the inverting output couples the corresponding signal having negative polarity into a second transmitting waveguide, so that both signals may overcouple into the receiving waveguide along the waveguides during the propagation time.

A respective resistor is preferably provided for terminating a free end of the radially distributed segments of the at least one transmitting waveguide and/or of the at least one receiving waveguide. In this way, in particular, the receiving waveguides are terminated reflection-free and may be considerably longer than the minimal wavelength $\lambda_{min}$ occurring in the signal, which may be calculated as the smallest relevant wavelength with the aid of $\lambda_{min} = c2\pi\tau$. This is due to the fact that interfering reflections may already occur in mismatched waveguides when their length is larger than approximately 1/10 of the maximal wavelength occurring in the signal. When a contactless data transmission is present, the waveguides are not longer than the smallest wavelength, but have a length of approximately 1/5 of the smallest relevant wavelength, so that these waveguides are no longer considerably shorter, and never longer than the smallest wavelength. Longer waveguides, in contrast, would result in a cross-talk of two adjoining bits.

According to one specific embodiment of the present invention, a resistive coupler is provided as the means for addition. This may be a resistive 50/50 coupler, for example, with the aid of which a signal having a high stability may be obtained, regardless of the angle of a twisting of the transmitter with respect to the receiver, in that the received signals of all segments of the receiving waveguide are added up.

The example device advantageously furthermore includes means for reconstructing the signal obtained by addition. This has the advantage that the transmitted signal, which is present in a pulse form at the receiver, may be reconstructed into the original rectangular signal. For this purpose, an integrator or a comparator with hysteresis is preferably provided as the means for reconstruction.

According to one preferred specific embodiment of the present invention, half rings are provided as segments for the at least one transmitting waveguide and/or for the at least one receiving waveguide. In this way, the advantages given according to the present invention are nonetheless achieved, at a comparatively low design complexity.

Furthermore, as an alternative, shortened receiving rings having opposing outcoupling points are provided as segments for the at least one transmitting waveguide and/or for the at least one receiving waveguide. This has the advantage that, in this way, shorter signal propagation times may be achieved, and thereby higher bit rates are made possible.

The length of the segments of the at least one receiving waveguide is advantageously larger than the minimal wavelength occurring in the signal to be transmitted. In this way, it may be achieved that the receiving waveguide may be designed to be considerably larger than in the case of implementations known from the related art, which results in a larger coupling surface, and thus in a higher coupling efficiency.

The example device according to the present invention furthermore makes it possible that the at least one transmitting waveguide is provided at a rotor, and the at least one receiving waveguide is provided at a stator.

According to one further specific embodiment of the present invention, it is provided that the device includes means for dividing the signal to be transmitted for a first transmitting waveguide and for a second transmitting waveguide. In this way, a waveguide rotary transmitter in a symmetrical design may be obtained, in which a signal is, for example, divided among two comparator inputs, one comparator coupling the signal into the left waveguide pair, and the other comparator coupling the signal into the right waveguide pair.

In such a specific embodiment, the device advantageously includes a first receiving waveguide and a second receiving waveguide, the first receiving waveguide being provided for detecting the signal transmitted with the aid of the first transmitting waveguide, and the second receiving waveguide being provided for detecting the signal transmitted with the aid of the second transmitting waveguide. In this way, signals may be obtained at the receiver side which, as a result of addition, form a symmetrical signal, from which the original rectangular data stream may be restored.

Advantageous refinements of the present invention described herein and shown in the figures.

BRIEF DESCRIPTION OF THE DRAWINGS

Exemplary embodiments of the present invention are described in greater detail based on the figures and the description below.

DETAILED DESCRIPTION OF EXAMPLE EMBODIMENTS

Figure 1:
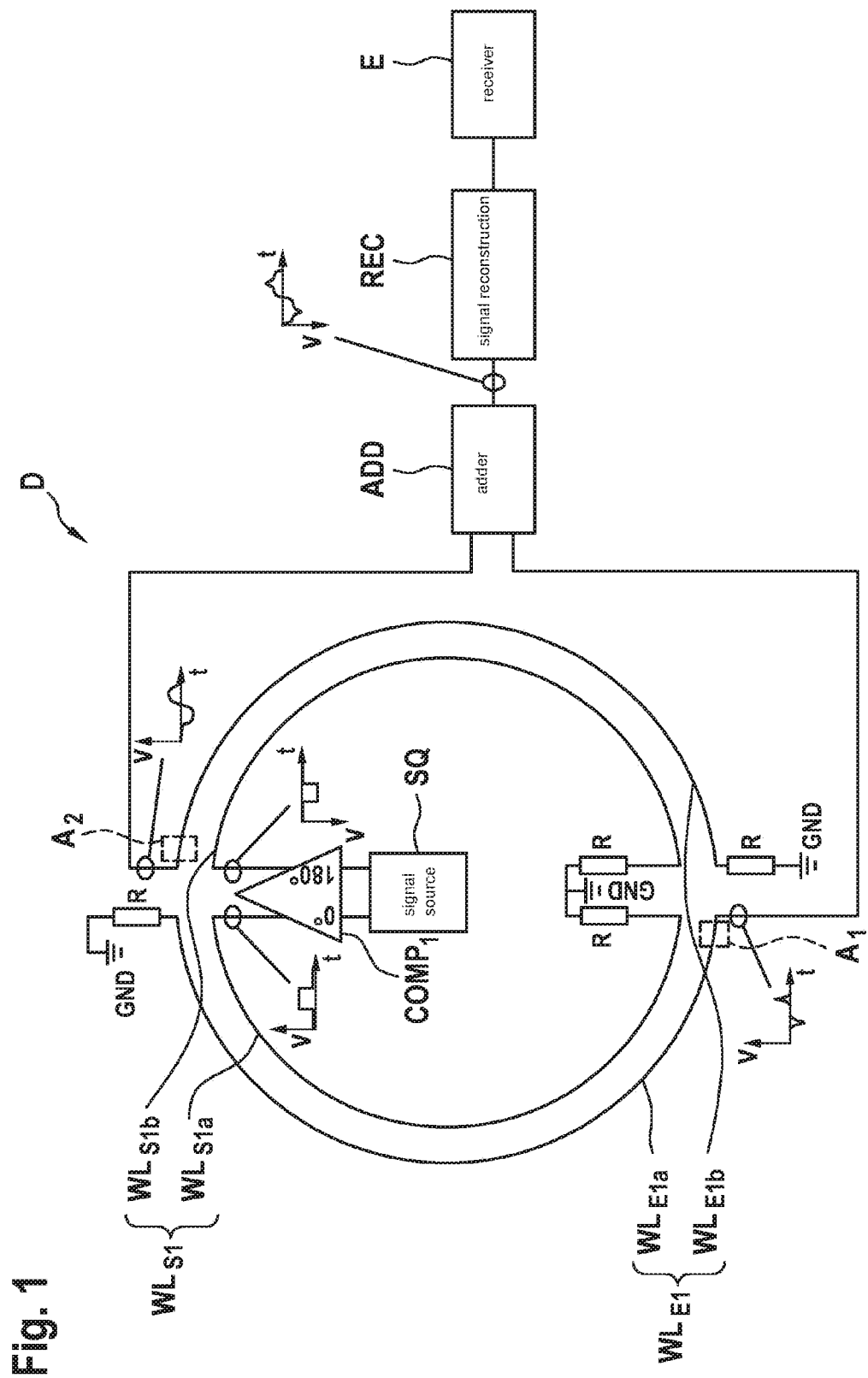
FIG. 1 shows a device according to the present invention according to a first exemplary embodiment.

FIG. 1 shows a device according to the present invention in the form of a waveguide rotary transmitter D according to a first exemplary embodiment, which is largely immune to unevenness and tilting. For this purpose, receiving waveguide $WL_{E1}$ is divided into multiple, radially distributed segments $WL_{E1a}$, $WL_{E1b}$, whose received signals are added up with the aid of an adder ADD.

If, for example, the receiving amplitude of a segment $WL_{E1a}$ is reduced due to a tilting or an unevenness, the receiving amplitude of the opposite segment $WL_{E1b}$ is high. By adding up the signals of all segments $WL_{E1a}$, $WL_{E1b}$ of receiving waveguide $WL_{E1}$, the amplitude of the result is rendered independent of the angular position, which makes a cumbersome readjustment of the signal amplitude at the receiver E unnecessary.

In the present example, corresponding to FIG. 1, segments $WL_{S1a}$, $WL_{S1b}$ of transmitting waveguide $WL_{S1}$ and segments $WL_{E1a}$, $WL_{E1b}$ of receiving waveguide $WL_{E1}$ are implemented as half rings. The signals which are coupled into one side of transmitting half rings $WL_{S1a}$, $WL_{S1b}$ are inverted with respect to one another. Termination resistors R are situated at the other side of transmitting half rings $WL_{S1a}$, $WL_{S1b}$.

Taps $A_1$, $A_2$ of segments $WL_{E1a}$, $WL_{E1b}$ of receiving waveguide $WL_{E1}$ are situated at opposite positions, the free end being terminated with a respective resistor R. In this way, segments $WL_{E1a}$, $WL_{E1b}$ of receiving waveguide $WL_{E1}$ are terminated reflection-free and may be considerably longer than the minimal wavelength $\lambda_{min}$ occurring in the signal. As a result of this design, the surface area is maximized via which the electromagnetic wave of transmitting wave guide $WL_{S1}$ may be overcoupled onto that of receiving waveguide $WL_{E1}$. This results in a high coupling efficiency, which renders a pre- or post-amplification of the signal unnecessary. At the same time, this system functions even at high data rates of typically 1 Gbit/s.

As is further shown in FIG. 1, a comparator $COMP_1$, which increases the edge steepness of the rectangular signal, is situated behind signal source SQ. Non-inverting output 0° couples a rectangular signal having positive polarity into left segment $WL_{S1a}$ of transmitting waveguide $WL_{S1}$, and inverting output 180° couples the corresponding signal having negative polarity into right segment $WL_{S1b}$ of transmitting waveguide $WL_{S1}$. Both signals propagate along segments $WL_{S1a}$, $WL_{S1b}$ of waveguide $WL_{S1}$ up to termination resistors R and, during the propagation time, couple over into segments $WL_{E1a}$, $WL_{E1b}$ of receiving waveguide $WL_{E1}$.

Tap $A_1$ at the left receiving waveguide is situated at the end of the propagation section of the input signal. An inverted, high-pass filtered signal is received. At the locations at which steep signal edges were present at the input signal, the output signal thus has narrow pulses.

Tap $A_2$ at right segment $WL_{E1b}$ of receiving waveguide $WL_{E1}$, in contrast, is situated at the start of the propagation section of the input signal. The output signal is made up of pulses which occur at the locations of signal edges of the input signal; the polarity of the signal, however, remains unchanged. The pulse width is greater than that of left segment $WL_{E1a}$ of receiving waveguide $WL_{E1}$ and corresponds to the sum of the propagation times of the input signal along right segment $WL_{S1b}$ of transmitting waveguide $WL_{S1}$ and of right segment $WL_{E1b}$ of receiving waveguide $WL_{E1}$.

During a twisting of the transmitter with respect to the receiver by 180°, the signals coupled out of segments $WL_{E1a}$, $WL_{E1b}$ of receiving waveguide $WL_{E1}$ are interchanged. A twisting dissimilar from 180°, in contrast, yields an overlapping of the long pulse and of the short pulse at each of segments $WL_{E1a}$, $WL_{E1b}$ of receiving waveguide $WL_{E1}$. The two received signals are added up, for example, via a resistive 50/50 coupler as means ADD for addition. The result is a signal which has a high stability, regardless of the angle of the twisting of the transmitter with respect to the receiver. The pulse-shaped signal is reconstructed into the original rectangular signal based on a means REC for signal reconstruction, for example in the form of an integrator or a comparator with hysteresis.

Figure 2:
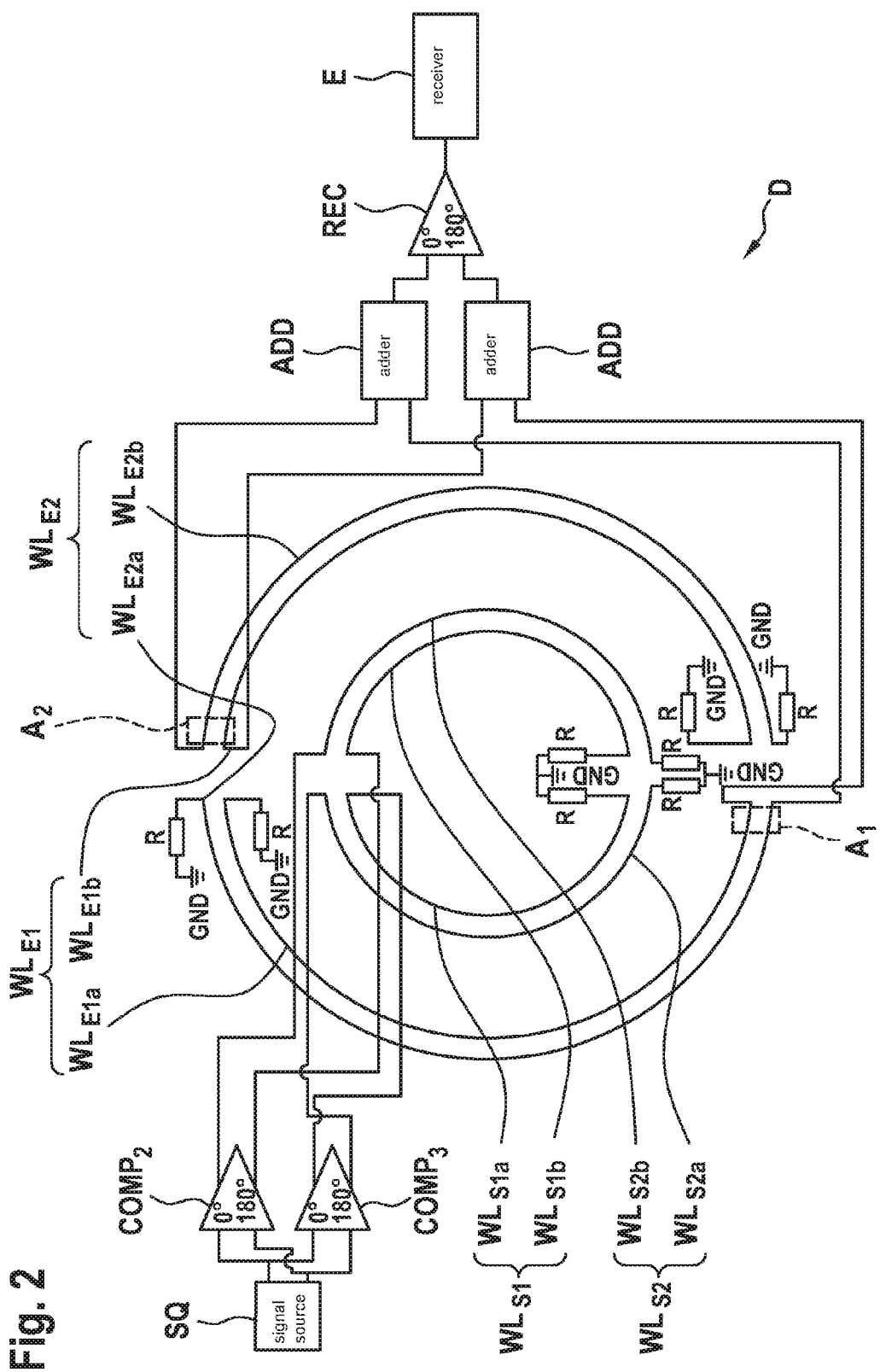
FIG. 2 shows a device according to the present invention in a symmetrical design according to a second exemplary embodiment.

FIG. 2 shows a device according to the present invention in a symmetrical design according to a second exemplary embodiment, configured as a waveguide rotary transmitter D. The input signal originating from signal source SQ is divided among inverting inputs 180° and non-inverting inputs 0° of two comparators $COMP_2$, $COMP_3$.

Comparator $COMP_3$, for example, couples the signal into the left waveguide pair, made up of segments $WL_{S1a}$, $WL_{S2a}$ of transmitting waveguides $WL_{S1}$ and $WL_{S2}$. Comparator $COMP_2$, in contrast, according to the exemplary embodiment couples the signal into the right waveguide pair, made up of segments $WL_{S1b}$, $WL_{S2b}$ of transmitting waveguides $WL_{S1}$ and $WL_{S2}$. A different wiring of the comparator outputs is also possible. As an alternative, according to the present invention the use of a fan-out buffer may also be provided.

On the receiver side, the two signals received at outer segments $WL_{E2a}$, $WL_{E2b}$ of the waveguides are added up by a means ADD for addition. Furthermore, similarly, the two signals received at inner segments $WL_{E1a}$, $WL_{E1b}$ of the waveguides are also added up by a means ADD for addition. The results of the two additions form a symmetrical signal, from which the original rectangular data stream is restored by a means REC for signal reconstruction, in the present example in the form of a comparator with hysteresis REC.

What is claimed is:

1. A device for transmitting a signal using waveguides in a rotating system, the device comprising:
   at least one transmitting waveguide;
   at least one receiving waveguide, each of the at least one receiving waveguide and the at least one transmitting waveguide being divided into multiple radially distributed segments, wherein the radially distributed segments of the at least one receiving waveguide each include a tap; and
   an adder configured to add together signals obtained using the taps of the radially distributed segments of the at least one receiving waveguide;
   wherein a length of each of the segments of the at least one receiving waveguide is greater than a minimal relevant wavelength $\lambda_{min}=c\Pi\tau$ occurring in the signal to be transmitted.

2. The device as recited in claim 1, further comprising:
   a reconstruction component configured to reconstruct a signal obtained by the addition by the adder.

3. The device as recited in claim 2, wherein the reconstruction component is an integrator or a comparator with hysteresis.

4. A device for transmitting a signal using waveguides in a rotating system, the device comprising:
   at least one transmitting waveguide;
   at least one receiving waveguide, each of the at least one receiving waveguide and the at least one transmitting waveguide being divided into multiple radially distributed segments, wherein the radially distributed segments of the at least one receiving waveguide each include a tap;
   an adder configured to add together signals obtained using the taps of the radially distributed segments of the at least one receiving waveguide; and
   a reconstruction component configured to reconstruct a signal obtained by the addition by the adder;
   wherein the reconstruction component is an integrator or a comparator with hysteresis.

5. The device as recited in claim 4, wherein the taps of the radially distributed segments of the at least one receiving waveguide are situated opposite one another.

6. The device as recited in claim 4, furthermore comprising:
   a component configured to couple the signal to be transmitted having positive polarity into a first segment of the at least one transmitting waveguide, and to couple the signal to be transmitted having negative polarity into a second segment of the at least one transmitting waveguide.

7. The device as recited in claim 6, the component is a comparator, which has a non-inverting output and an inverting output.

8. The device as recited in claim 4, wherein a respective resistor is provided for terminating a free end of each of the radially distributed segments of the at least one transmitting waveguide and/or each of the radially distributed segments of the at least one receiving waveguide.

9. The device as recited in claim 4, wherein the adder is a resistive coupler.

10. The device as recited in claim 4, wherein the radially distributed segments of the at least one transmitting waveguide and/or the radially distributed segments of the at least one receiving waveguide, are half rings.

11. The device as recited in claim 4, wherein the radially distributed segments of the at least one transmitting waveguide and/or the radially distributed segments of the at least one receiving waveguide, are shortened receiving rings having mutually opposing decoupling points.

12. The device as recited in claim 4, wherein the at least one transmitting waveguide is provided at a rotor, and the at least one receiving waveguide is provided at a stator.

13. The device as recited in claim 4, further comprising:
a component configured to divide the signal to be transmitted for a first transmitting waveguide and for a second transmitting waveguide.

14. The device as recited in claim 13, furthermore comprising:
a first receiving waveguide and a second receiving waveguide, the first receiving waveguide provided for detecting the signal transmitted using the first transmitting waveguide, and the second receiving waveguide being provided for detecting the signal transmitted with using the second transmitting waveguide.

* * * * *